(12) United States Patent
Talamonti

(10) Patent No.: US 7,789,854 B2
(45) Date of Patent: Sep. 7, 2010

(54) MEDICAL TREATMENT KIT AND METHODS OF USE THEREOF

(76) Inventor: Anthony R. Talamonti, 1710 41$^{st}$ Ave., Kenosha, WI (US) 53144

( * ) Notice: Subject to any disclaimer, the term of this patent is extended or adjusted under 35 U.S.C. 154(b) by 0 days.

(21) Appl. No.: 11/127,589

(22) Filed: May 12, 2005

(65) Prior Publication Data

US 2007/0005027 A1   Jan. 4, 2007

Related U.S. Application Data

(60) Provisional application No. 60/570,716, filed on May 13, 2004.

(51) Int. Cl.
*A61M 37/00* (2006.01)
(52) U.S. Cl. .......................... 604/90; 604/416
(58) Field of Classification Search ............... 604/416, 604/410, 310, 306, 290, 518, 87, 82, 3, 89, 604/90; 222/129; 206/219
See application file for complete search history.

(56) References Cited

U.S. PATENT DOCUMENTS

| | | | | |
|---|---|---|---|---|
| 3,163,163 A | * | 12/1964 | Wilburn | 206/221 |
| 3,190,619 A | | 6/1965 | Penney et al. | |
| 3,842,836 A | * | 10/1974 | Ogle | 604/416 |
| 4,062,477 A | * | 12/1977 | Morane | 222/129 |
| 4,330,531 A | * | 5/1982 | Alliger | 424/661 |
| 4,850,966 A | * | 7/1989 | Grau et al. | 604/82 |
| 4,950,237 A | | 8/1990 | Henault et al. | |
| 5,383,579 A | * | 1/1995 | Lanfranconi et al. | 222/129 |
| 6,283,933 B1 | * | 9/2001 | D'Alessio et al. | 604/3 |
| 6,811,341 B2 | * | 11/2004 | Crane | 401/134 |
| 2001/0047162 A1 | | 11/2001 | Yugari | |
| 2004/0039366 A1 | * | 2/2004 | MacLeod | 604/416 |
| 2004/0060831 A1 | | 4/2004 | De Laforcade | |

FOREIGN PATENT DOCUMENTS

| | | |
|---|---|---|
| EP | 0812775 | 12/1997 |
| EP | 1174355 | 1/2002 |
| GB | 1216452 | 12/1970 |

OTHER PUBLICATIONS http://www.uni-patch.com/PDF/UseFrangible.pdf.
http://www.inge.it/eng/produz-eng-separaliqliq.htm.

* cited by examiner

*Primary Examiner*—Nicholas D Lucchesi
*Assistant Examiner*—Laura A Bouchelle
(74) *Attorney, Agent, or Firm*—Reinhart Boerner Van Deuren s.c.

(57) ABSTRACT

A medical treatment kit and methods of use thereof is provided. The kit includes a container, two or more chambers within the container, an antiseptic agent disposed in one of the chambers, a cleansing agent disposed in a separate chamber and an applicator. The agents are not contacted until immediate use of the kit is required. The medical treatment kit is used to administer an antiseptic shampoo or other medical composition to a patient with an open wound or injury. The kit is designed to be simple to use in an emergency situation. The kit is also designed to deliver medical compositions that are at the peak of potency.

18 Claims, 10 Drawing Sheets

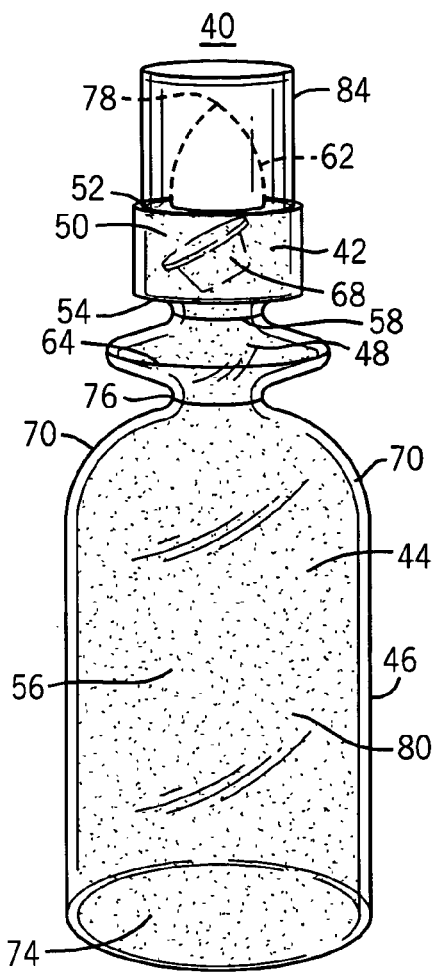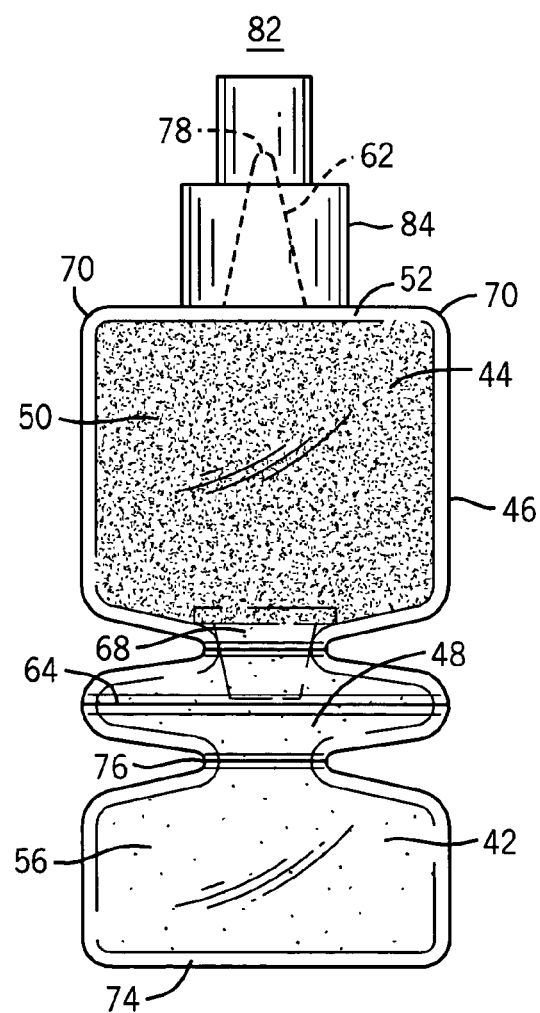

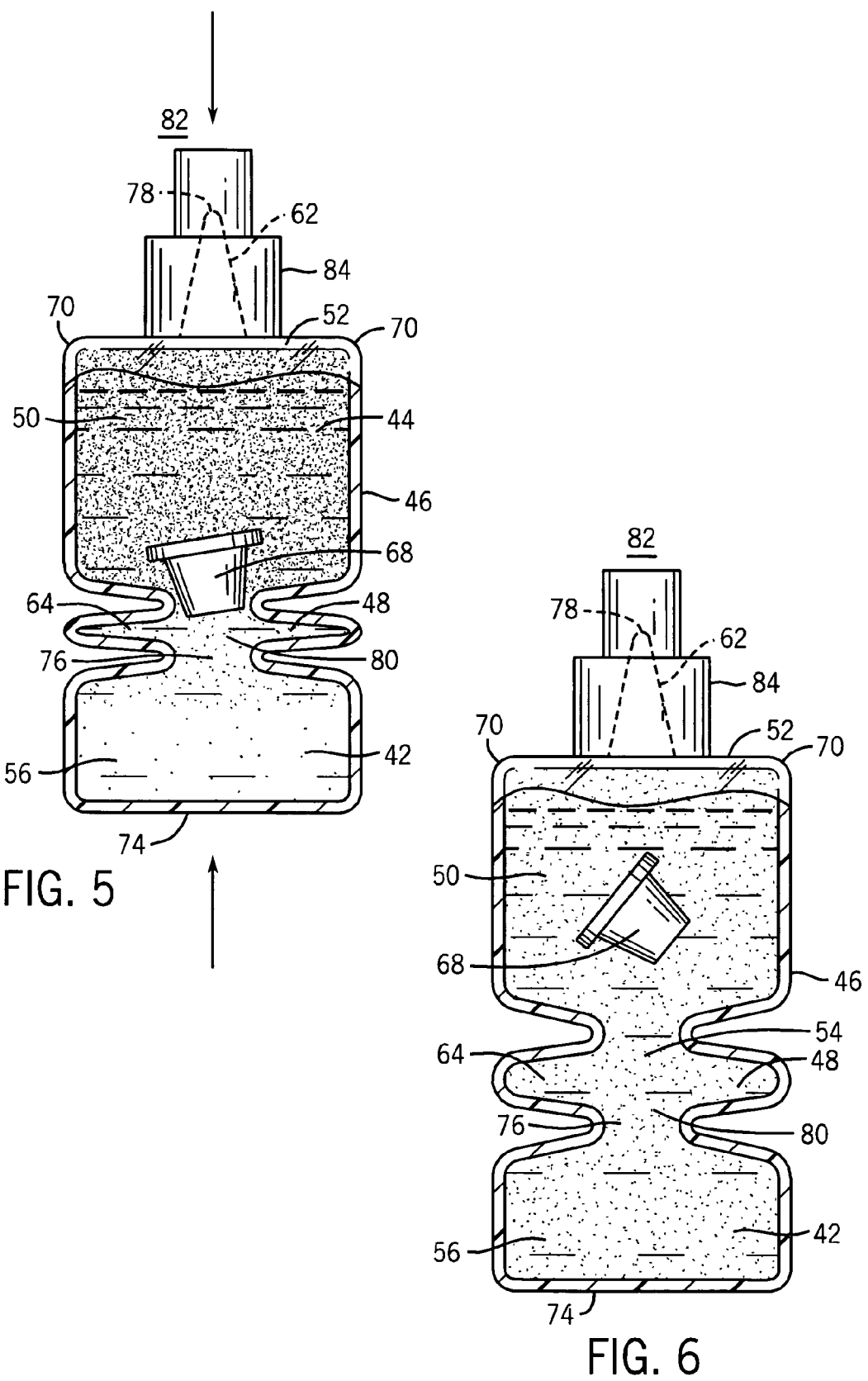

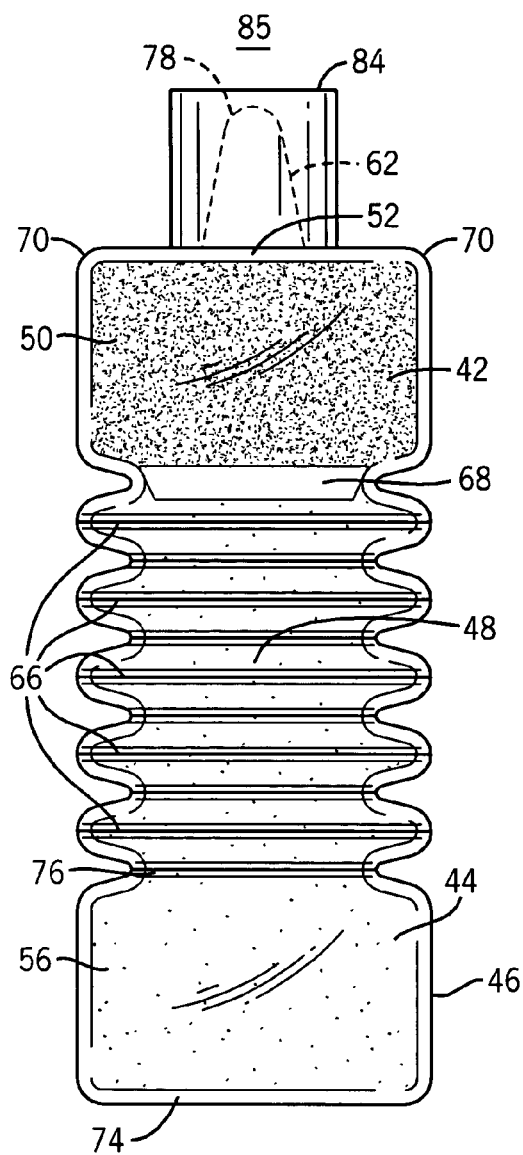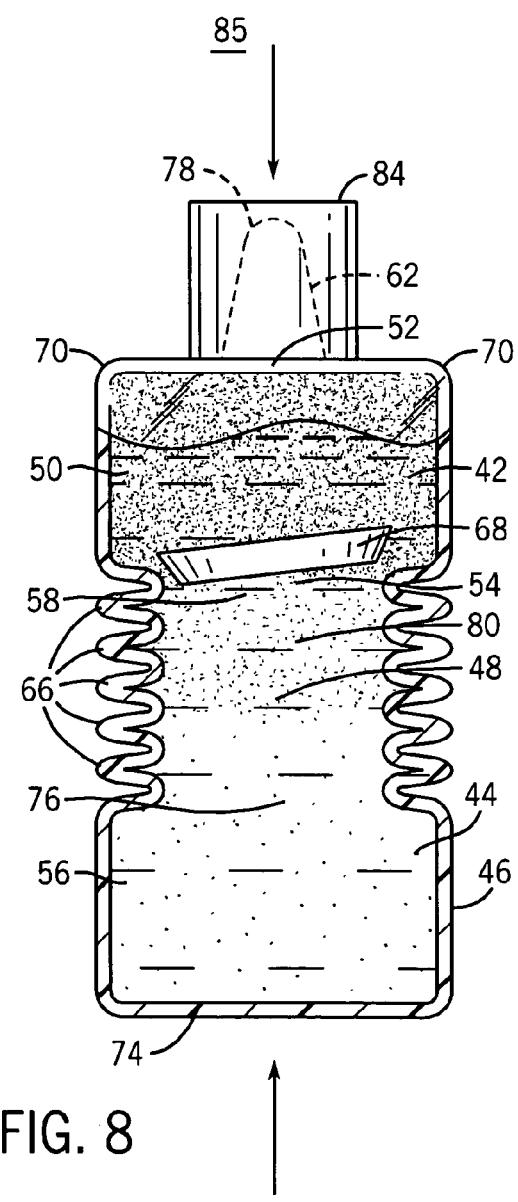
FIG. 7
FIG. 8

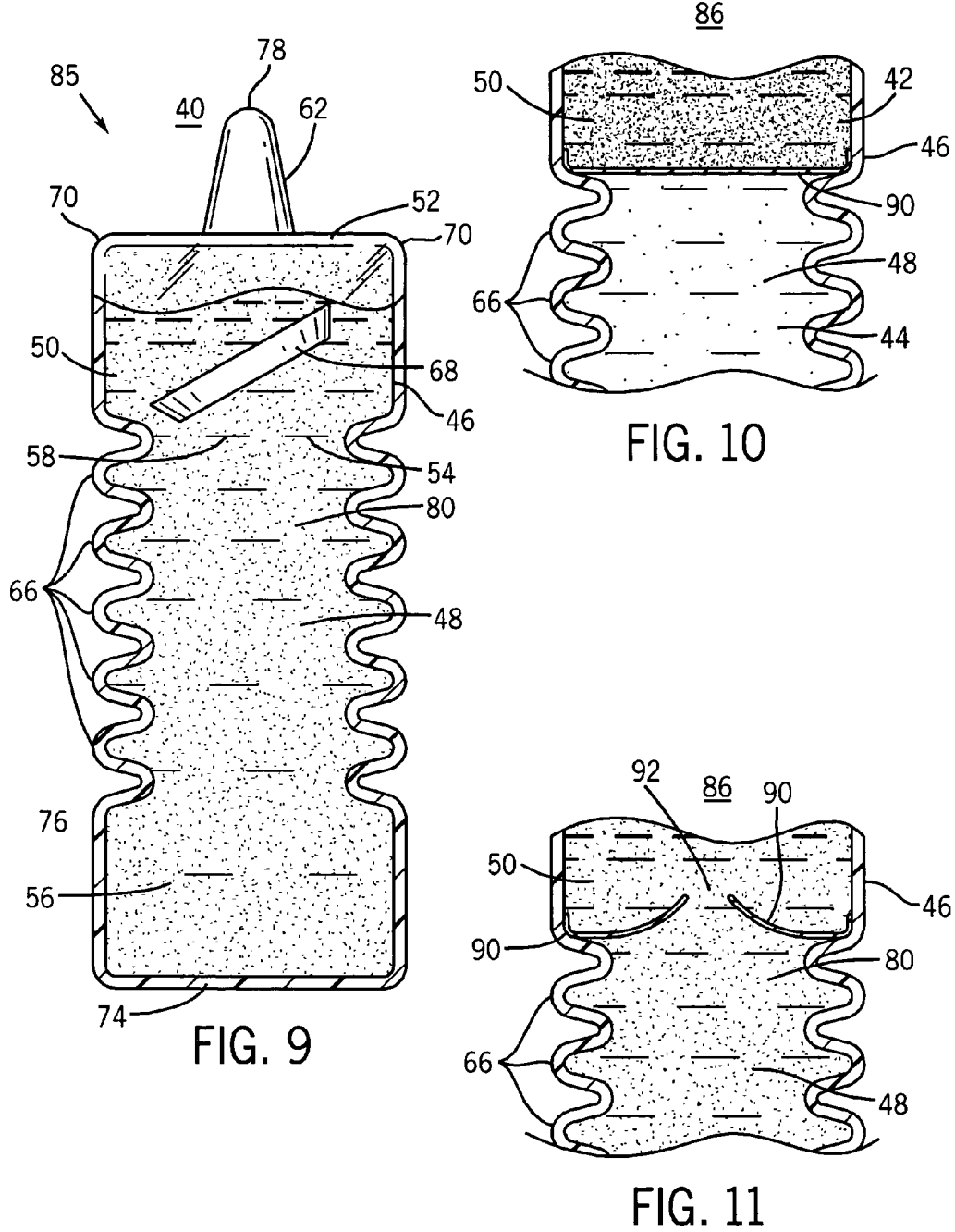

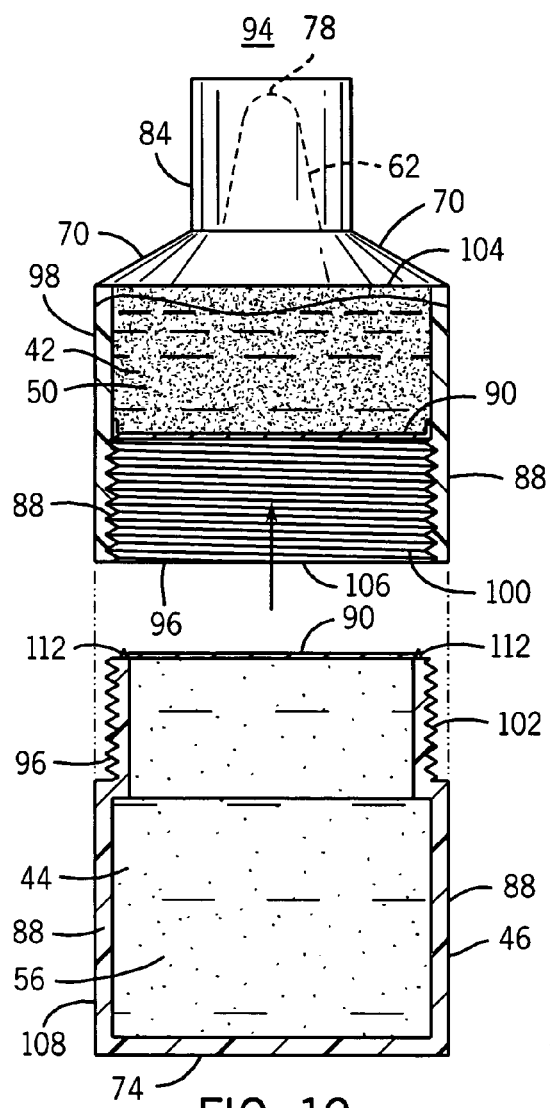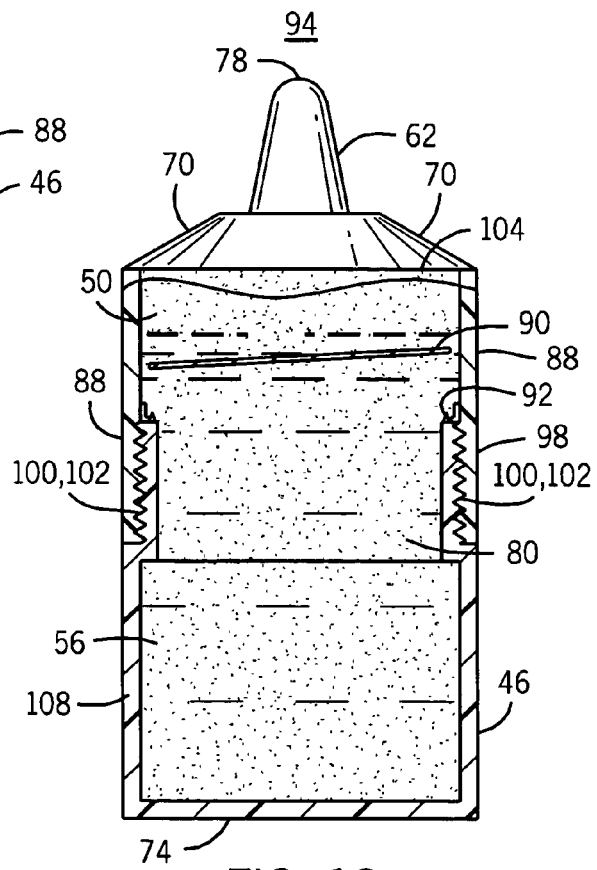
FIG. 12
FIG. 13

MEDICAL TREATMENT KIT AND METHODS OF USE THEREOF

CROSS-REFERENCE TO RELATED APPLICATIONS

This application claims priority benefit of provisional application Ser. No. 60/570,716 filed May 13, 2004, the entirety of which is incorporated herein by reference.

BACKGROUND OF THE INVENTION

Field of the Invention

The present invention relates generally to medical sanitation and more particularly, a medical treatment kit and method for packaging, delivering, using and applying a blood removal shampoo with sterilizing, anti-infective and/or antiseptic properties.

In the current medical environment, time is usually of the essence, especially in emergency situations. In treating wounds, one important step is to clean the wound as quickly as possible. One method is to clean the wound first with an antiseptic agent and then attempt to clean the wound with a cleaning agent. This is a two step process which can be costly in terms of time particularly in situations where many people in need of treatment.

Another method of treating wounds is to measure a small quantity of an antiseptic agent and mix it with a small quantity of a cleansing agent and apply the mixture to the wound. Again, this method is costly in terms of the time needed to accurately pre-measure ingredients and then integrate the agents.

A further method is to have a cleansing and antiseptic agent prepared ahead of time. This method is costly if the shelf life of the mixed agents is best measured in minutes rather than hours or days. This may result in mixtures that are unusable. This is costly in terms of money.

Yet another method is to have a pre-mixed cleansing and antiseptic agent. These agents when mixed and stored have a limited shelf life. Again, this approach is economically disadvantageous.

The present invention addresses these problems by providing a medical treatment kit that provides an economical and efficient method of treating wounds. Each kit includes a container divided into at least two isolated chambers. One chamber has a cleaning agent; the other has a antiseptic agent. The chambers are separated or isolated to prevent premature mixing of the agents. This separation is designed as a temporary basis, primarily for storage purpose. The isolation is designed to be quickly and easily removed such that the kit can be used in time critical situations. Once the isolation is removed, the amalgamation of the two agents is effortlessly done, providing a potent antiseptic shampoo that can treat and clean wounds.

Thus, it is an objective of the present invention to provide a medical treatment kit for cleansing and treating a wound that can be easily dispensed without requiring a pre-mixed composition. It is a related objective of the present invention to create a uniform antiseptic shampoo from a cleansing agent and antiseptic agent provided in isolated/separated chambers and that do not mix or contact each other until expressly needed by the medical professional.

It is another objective of the present invention to have cleansing and antiseptic agents that are provided in pre-measured quantities, for example, in therapeutically and/or clinically effective quantities, and separately stored in a single container in order to save preparation time during a medical emergency.

It is another objective of the present invention to provide a medical treatment kit for cleaning and treating wounds that uses medical agents that are relatively inexpensive compared to other currently available methods and treatment kits.

It is a further objective of the present invention to provide a method for quickly cleansing and treating a wound by providing a medical treatment method that is easy to implement and carry out in an emergency situation. It is a further objective of the present invention to provide a method of storing medical compositions for later application by a user in which mixing or contacting of the separate medical compositions does not occur until required by the user.

The medical treatment kit of the present invention must also be of construction which is both durable and have a long shelf life, and it should also require little or no maintenance to be provided by the user throughout its storage lifetime. In order to enhance the market appeal of the medical treatment kit of the present invention, it should also include inexpensive medical agents to thereby afford it the broadest possible market. It is also an objective that all of the aforesaid advantages and objectives be achieved without incurring any substantial relative disadvantage.

SUMMARY OF THE INVENTION

The disadvantages and limitations of the background art discussed above are overcome by the present invention. With this invention, a medical treatment kit and methods of use thereof for treating wounds and/or other topical, medical or therapeutic applications is provided.

The present invention provides, in part, a medical treatment kit that is easy to implement and carry out in an emergency or non-emergency and is economical. The medical treatment kit of the present invention typically contains two medical agents: a cleansing agent and an antiseptic agent that are isolated from each other until the combination of such agents is required.

The preferred cleansing agent of the kit is a shampoo. However any detergent, soap, solvent and/or surfactant known to those skilled in the art may be used. The preferred antiseptic agent of the medical treatment kit is hydrogen peroxide ($H_2O_2$). Other antiseptic agents can include other disinfecting agents, such as alcohol, as will be well known to those skilled in the art.

If desired, an odor-controlling agent, such as baking soda, is added. Further, additional compositions can be used in the medical treatment kit. For example, antibacterial agents, lotions, skin protectants, moisturizing agents, drying agents, anti-inflammatory agents, anti-infective agents, creams, ointments, powders, solutions, gels, symptom-relieving agents and/or other compositions known in the art, may be included or utilized with the kit.

In accordance with the present invention, the cleansing and antiseptic agents are provided in pre-measured quantities and placed in two isolated chambers. The medical agents are properly isolated such that they do not prematurely mix, combine and/or otherwise interact until required by the user. However, the medical agents are placed in proximity to each other such that when needed, the medical agents are readily available to mix and interact. Once combined, an antiseptic shampoo is created.

Immediately after combination, the antiseptic shampoo is at its peak of potency, and therefore, the most clinically/therapeutically effective. Accordingly, the present invention provides a method of delivering an antiseptic shampoo in which the combination of agents is at its maximum effectiveness/potency at the time its use is required. Also, since the medical agents are initially separated and only mixed when needed, more economical cleansing and antiseptic agents can be used to achieve the desired cleansing effect. In addition, as isolated agents, the medical kit of the present invention exhibits an extended shelf life.

In the preferred embodiment, the antiseptic shampoo loosens and removes coagulated blood and has antibacterial properties. This antiseptic shampoo also cleans the wound and hair of blood, debris and other contaminants. In certain embodiments, an odor-controlling agent, such as baking soda, is added.

The medical treatment kit can include a multi-chamber bottle that contains a pre-measured amount of one or more cleansing agents in one chamber of the bottle, and a pre-measured amount of one or more antiseptic agents in another chamber. The bottle also contains a stopper or a separation mechanism to prevent the two medical agents from mixing or integrating until required by the user. The stopper is positioned between one of the aforementioned chambers and a third chamber that contains a flexible bellow(s). This allows the user to apply vertical pressure, thereby releasing the stopper from the frictional seal. The user can then shake the contents of the bottle to form an integrated/combined cleansing and antiseptic agent—an antiseptic shampoo. The antiseptic shampoo is released through an outlet or nozzle on one end of the bottle. The applicator is placed close to the wound. The rate of flow of the antiseptic shampoo is easily proportionately controlled by the pressure exerted on the bottle and the size of the applicator.

In another embodiment, the present invention provides a bottle that has a main container section divided into two or more chemically isolated chambers or columns. The cleansing agent is contained in one chamber and the antiseptic agent is contained in the other chamber. Within the container, a foil membrane separates the two chambers of the container, forming a barrier, which prevents the two medical agents from mixing or reacting until required by the user. This foil membrane is also connected to the cap of the container. When the medical treatment kit is needed, the cap of the container is removed; thereby breaking the foil membrane or seal and allowing the cleansing agent and the antiseptic agent to mix as the two medical agents flow through an outlet of the container.

In yet another embodiment, the container has two physically separated chambers, one chamber with male threads, the other with female threads. At least one of the containers has a protective foil membrane over these openings. When the two chambers are screwed together, a small blade mounted on one of the chambers cuts the foil membrane on the other chamber. The two medical agents are combined by shaking to form an antiseptic shampoo.

In certain other embodiments, the present invention includes a container which is a foil pouch that is separated into two foil chambers. Each chamber has a formed outlet or nozzle for releasing the contents of each respective chamber. Across each nozzle there is a tear strip. In one embodiment, the two nozzles share a common tear strip. When the medical treatment kit is needed, the tear strip(s) is torn off allowing the cleansing agent and the antiseptic agent to be mixed within the stream as they flow through the applicator. The two medical agents can be further mixed by the user by hand, creating an antiseptic shampoo. The antiseptic shampoo is then directed to the wound via the applicator of the medical treatment kit.

The present invention can also be, in part, a method of quickly and efficiently cleaning/treating a wound using a medical kit. This method includes providing a pre-measured amount of an antiseptic agent disposed in an enclosure and a pre-measured amount of a cleansing agent disposed in a separate enclosure, wherein the antiseptic agent and cleansing agent do not contact each other until just before the kit is used.

The two agents are mixed together by shaking or massaging the container to form an enhanced antiseptic shampoo. Any protection devices, such as a cap, are removed to expose the applicator. The applicator is then directed to a wound or injured area. Proper pressure is applied to the container to dispense the proper amount of the admixture (antiseptic shampoo) needed to the wound or injured area.

It may therefore be seen that the present invention teaches both a medical treatment kit and a method to treat a wound by providing an antiseptic shampoo that can be quickly and easily prepared and dispensed when needed by the medical professional.

The medical treatment kit of the present invention is of a construction which is both durable and long lasting, and which will require little or no maintenance to be provided by the user throughout its operating lifetime. The medical treatment kit of the present invention is also of inexpensive construction to enhance its market appeal and to thereby afford it the broadest possible market. Finally, all of the aforesaid advantages and objectives are achieved without incurring any substantial relative disadvantage.

DESCRIPTION OF THE DRAWINGS

These and other advantages of the present invention are best understood with reference to the drawings, in which:

FIG. 3 is a side view of the medical treatment kit illustrated in FIGS. 1 and 2 showing the two agents mixed and/or integrated into one composition;

FIG. 4 is a side view of an alternate embodiment of a medical treatment kit of the present invention in which the ratio of volume of the lower chamber to the upper chamber is less than 1.0 and having a bellowed chamber with one bellow;

FIG. 5 is a side view of the medical treatment kit illustrated in FIG. 4 being vertically squeezed to release a stopper to integrate the agents;

FIG. 6 is a side view of the medical treatment kit illustrated in FIGS. 4 and 5 showing the two agents mixed and/or integrated;

FIG. 7 is a side view of an additional embodiment of a medical treatment kit of the present invention in which the ratio of volume of the lower chamber to the upper chamber is approximately 1.0 and having a bellowed chamber with several bellows;

FIG. 8 is a side view of the medical treatment kit illustrated in FIG. 7 shown being vertically squeezed to release a stopper to integrate the agents;

FIG. 9 is a side view of the medical treatment kit illustrated in FIGS. 7 and 8 shown with the two agents mixed and/or integrated;

FIG. 10 is a partial side view of a container using foil as a barrier/membrane;

FIG. 11 is a partial side view of the membrane illustrated in FIG. 10 showing the ruptured membrane;

FIG. 12 is a side view of another embodiment of a medical treatment kit of the present invention illustrating two separate chambers spaced apart by a barrier portion;

FIG. 13 is a side view of the medical treatment kit illustrated in FIG. 12 showing the two chambers screwed together, causing foil between the two chambers to tear and/or break allowing two agents to integrate and/or mix;

DETAILED DESCRIPTION OF THE PREFERRED EMBODIMENT

Figure 1:
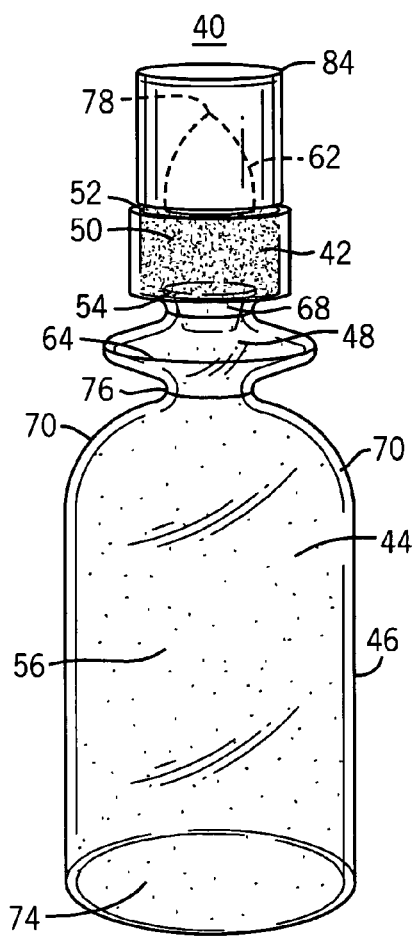
FIG. 1 is a side view of a medical treatment kit in bottle form where the ratio of volume of the lower chamber to the upper chamber is much larger than 1.0 and having a bellowed chamber with one bellow.

With this invention, a medical treatment kit 40 is shown including one or more medical treatment, cleansing and/or antiseptic agents 42 and 44 for use in the method of the present invention. Referring first to FIG. 1, a medical treatment kit 40 includes a bottle 46 having a first chamber 50 and a second chamber 56 and a middle diaphragm 48 disposed therebetween.

The bottle 46 is preferably the size of a common 12 oz. soda can; however, any size bottle may be used depending on the given end-use application. The first and second chambers 50 and 56 are hermetically sealed and designed to contain medically proportioned agents 42 and 44, as will be described in more detail herein.

Since some of the compositions included within the bottle are highly reactive, the medical treatment kit 40 is preferably constructed of one or more layers of a material that is opaque such as HDPE (High Density Polyethylene). The bottle 40 is also opaque to prevent the premature breakdown of the stored chemicals from light. Accordingly, the bottle 46 can be constructed of any thermoplastic material (polypropylene, low density polyethylene, polystyrene, AS, ABS, methacrylate, etc.) or other material, and specifically those approved by the FDA for use in the given medical application, as will be known to those skilled in the art. Where light sensitivity of the contents is not an issue, the container may be constructed of a transparent or substantially transparent material.

The first or top chamber 50 is designed to be filled at or near to capacity with one or more medical agents or compositions 42 or 44. In the preferred form, the shape of the chamber is cylindrical as shown in FIGS. 1-6. However, the first chamber may be of any size or shape. A bottom radial surface 54 of the first chamber is attached to the bellowed middle diaphragm 48. The bottom radial surface 54 is partially open providing an opening in order to physically adapt to the mating bellow 64 of the middle diaphragm 48. A top radial surface 52 of the first chamber (when the bottle 46 is being stored) is also partially open to allow the contents of the bottle 46 to exit the bottle 46 via an attached applicator 62, outlet, nozzle or opening.

The applicator 62 of the bottle is coupled to the top radial surface 52 of the first or top chamber 50. The applicator 62 is taller than it is wider. There is an opening 78 at the top of the applicator 62 to allow the antiseptic shampoo 80 to be dispensed from the medical treatment kit 40. The applicator 62 provides control and focus for the application of the contents of the kit 40. Thus, the opening 78 within the applicator 62 allows the contents of the kit 40 to exit the bottle 46 and be applied to a wound with the proper amount of pressure exerted on the bottle 46.

Preferably, there is cap 84 or other sealing mechanism over the opening in the applicator 62 to protect the applicator 62 from contamination and damage from external forces. The cap 84 can be screw-off or pop-off. In addition, a sealing mechanism such as foil, plastic or paper or other items known in the art may be used to cover the opening in the applicator 62.

Figure 2:
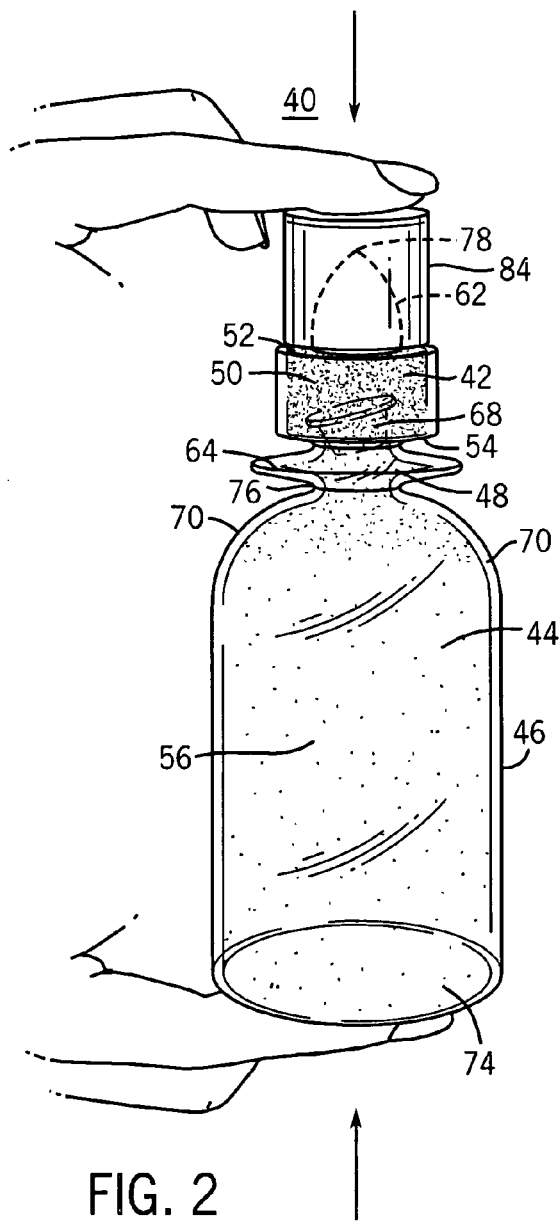
FIG. 2 is side view of the medical treatment kit illustrated in FIG. 1 shown being vertically squeezed to release a stopper to integrate the agents.

The second or bottom chamber 56 is substantially similar to the first chamber 50. The second chamber 56 can be of any shape, however in the preferred embodiment, the shape is cylindrical. In FIGS. 1-3 the volume ratio of the second chamber 56 to the first chamber 50 is much larger than 1.0. In FIGS. 4-6, the volume ratio of the second chamber 56 to the first chamber 50 is smaller than 1.0. In FIGS. 7-9, the volume ratio of the two chambers 50 and 56 is approximately 1.0. Thus, the first and the second chambers 50 and 56 may be of any size required by the particular agents 42 and 44 utilized and/or the end use application of the medical treatment kit 40.

The second chamber 56 is designed to be filled at or near to capacity with one or more medical agents or compositions. Shoulders 70 are formed at the top of the second chamber 56 to allow better transfer of the agent(s) 42 and/or 44. A top radial surface 76 of the second chamber 56 is partially open, forming an opening that will permit the contents of the second chamber 56 to mix with the contents of the first chamber 50 when called for by the user. A bottom radial surface 74 of the second chamber 56 encloses the contents and the surface is slightly curved toward the inside of the bottle 46. This allows the contents of the chamber to remain inside the second chamber 56, allowing the bottle 46 to stand on end as well as accept increased pressure when the bottle 46 is squeezed.

In between the first and the second chambers 50 and 56 is the accordion-like or bellowed middle diaphragm 48. This middle diaphragm 48 can have a single bellow 64 or rib as shown in FIGS. 1-6 or has multiple bellows 66 or ribs as shown in FIGS. 7-9. These bellows 66 allow the bottle 46 to be squeezed vertically with less effort. The middle diaphragm 48 separates the contents of each of the two chambers 50 and 56 such that the contents do not interact or contact each other until required by the user. The middle diaphragm 48 also provides a mechanism to release a stopper 68 which separates the two medical agents 42 and 44, as will be described in more detail below. Once needed, the middle diaphragm 48 bridges the contents of the two chambers 50 and 56.

The friction-secured stopper 68 has a slight conic shape and is positioned between the first and second chambers 50 and 56 as best illustrated in FIG. 1. The middle diaphragm 48 and the stopper 68 separate the first and second chambers 50 and 56, thereby preventing the medical agents 42 and 44 from contacting and/or interacting until required or needed by the user. Preferably, the stopper 68 is inserted such that the stopper 68 borders the top chamber 50 and the middle diaphragm 48 and the narrow portion of the stopper 68 is pointing down, as shown in FIGS. 1-9.

The medical agent included within the first chamber is preferably a pre-measured cleansing agent 42, and the medical agent included within the second chamber is preferably a pre-measured antiseptic agent. Preferably, the cleansing agent 42 is a shampoo and the antiseptic agent 44 is hydrogen peroxide ($H_2O_2$). Preferably, the hydrogen peroxide is provided in an about concentration of 2% to about 4% solution. The cleansing agent can include any soap, detergent, solvent, surfactant or combination thereof known to those skilled in the art, depending on the type of wound to be treated and/or the end-use medical application. In certain embodiment, the type of cleansing agent used is mild, for example, similar to a baby shampoo. The antiseptic agent can include any disinfectant composition known to those skilled in the art including, but not limited to, alcohol, witch hazel, iodine, mercurochrome, and/or other combinations thereof. The cleansing agent and the antiseptic agent are preferably provided in premeasured quantities and concentrations such that the resulting admixture is clinically and/or therapeutically effective upon contact with the wound, as will be well known to those skilled in the art.

In certain embodiments of the present invention either the cleansing agent or the antiseptic agent or both can include an odor-controlling agent, such as baking soda. Consistent with the broader aspects of the present invention, agents such as other odor-controlling agents, antibacterial agents, skin protectants, moisturizing agents, drying agents, anti-inflammatory agents, anti-infective agents, symptom-relieving agents, sterilizing agents, therapeutic agents, and/or combinations thereof, may be included or provided with the kit 40, as will be well known to those skilled in the art.

In addition, an inert ingredient(s) or delivery vehicles can be added to the medical agents. The type and quantity of the vehicle determines the consistency of the medical agent compound. The vehicle also controls whether or not the medical agent or composition penetrates the skin. Vehicles for delivery of the medical agents can include, but are not limited to, ointments, creams, lotions, solutions, powders, gels or any other vehicle known in the art.

It will be readily apparent to those skilled in the art that the medical kit and methods of the present invention can be utilized with a wide range of medicants, therapeutic and/or treatment compositions, depending on the type of wound or type of medical, cosmetic, nutritional, clinical or therapeutic application. Further, the duel chamber bottles/kits illustrated herein may be utilized in many additional chemical, pharmaceutical and/or nutritional applications, as will also be readily apparent to those skilled in the art.

When the medical treatment kit 40 as shown in FIGS. 1, 4, and 7 is needed, the bottle 46 is vertically squeezed (with pressure applied to both the top and bottom) as shown in FIGS. 2, 5, and 8; the stopper 68 is released from the middle diaphragm 48 as shown in FIGS. 3, 6 and 9. FIGS. 3, 6 and 9 show the stopper 68 moving to the chamber closest to the applicator 62 when implemented or squeezed. In certain other embodiments (not shown), the stopper 68 can move to the chamber furthest from the applicator 62 when implemented or squeezed. In either scenario, when the bottle 46 is squeezed, the stopper 68 dislodges, the two chambers 50 and 56 become connected. This allows the two medical agents 42 and 44 to mix and/or contact each other.

To utilize the medical treatment kit 40 of the present invention, the user shakes the bottle 46 for several seconds. This will completely blend the two medical agents 42 and 44—forming an antiseptic shampoo 80. The bottle 46 is inverted and the antiseptic shampoo 80 may now be applied to a medically contaminated part of the body where dirt and dried blood need to be removed. The bottle 46 is squeezed around the circumference of the bottle 46. The antiseptic shampoo 80 flows through the applicator 62 onto the wound. The rate of flow through the applicator 62 can be controlled by the squeezing or the pressured applied to the medical treatment kit 40, the size of the opening in the applicator 62 and the viscosity of the medical agents 42 and 44 contained therein. The squeezing action precisely and proportionately controls the amount of antiseptic shampoo 80 that is applied to the wound.

Referring to FIGS. 10-11, a second medical treatment kit 94 for use in the methods of the present invention is illustrated. A bottle 46 similar to the bottle 46 previously described is provided. However, the method of isolation of the chambers 50 and 56 is a membrane or foil 90 mounted on one of the bellows or rib(s) of the middle diaphragm 48, as shown in FIG. 10. The two chambers 50 and 56 of the bottle 46 contain separated quantities of a cleansing agent 42 and an antiseptic agent. The cleansing agent 42 and/or the antiseptic agent may be any one or more of those described herein.

Similar to the bottle 46 described with reference to FIGS. 1-9, top and bottom chambers 56 of the bottle 46 can be of any shape, and are preferably cylindrical. Top and bottom radial surfaces 106 contained in the top chamber 50 are partially open and each contain an opening. The bottom radial surface 54 of the top chamber 50 is attached to a bellowed middle diaphragm 48.

Attached to the top radial surface 52 of the top chamber 50 is an applicator 62, outlet, nozzle or opening. The applicator 62 is normally taller than it is wide. There is a small opening 78 at the top of the applicator 62 to allow the application of the antiseptic shampoo 80 from the medical treatment kit 94. When the need for the kit 94 arises and the contents of the kit 94 are mixed, the applicator 62 provides control and focus for the application of the contents of the kit 94. The opening 78 in the applicator 62 allows the contents of the kit 94 to exit and be applied to a wound. Also, as stated herein, the applicator 62 may optionally have a cap 84 or some other sealing device known in the art for protection.

The bottom chamber 56 has a top radial surface including an opening and a closed bottom radial surface 106. The top radial surface of the bottom chamber 56 is attached to the bellowed middle diaphragm 48. Thus, the two chambers 50 and 56 containing the selected medical agents 42 and 44 are separated by the bellowed middle diaphragm 48 as described herein.

In this configuration, foil 90 or a barrier membrane is attached to one of the bellow 66 or ribs in the bellowed middle diaphragm 48 horizontally, as shown in FIG. 10. The foil 90 prevents the medical agents 42 and 44 from mixing, contacting and/or reacting until required or needed by the user.

When use of the medical treatment kit is required, the bottle 46 is vertically squeezed. In this configuration, the membrane will rip or tear away 92 from the supporting rib of the middle diaphragm 48 as shown in FIG. 11. The two chambers 50 and 56 containing the medical agents 42 and 44 will then be connected, allowing the agents 42 and 44 to contact and mix. The bottle can then be shaken for several seconds which will completely blend the medical agents 42 and 44—forming an antiseptic shampoo 80, or other desired admixture/composition. The application of the antiseptic shampoo 80 is applied to the wound by turning the medical treatment kit 94 upside down and squeezing the bottle 46. This allows the antiseptic shampoo 80 to exit through the applicator 62, which is applied at a controlled rate to the wound.

Referring next to FIGS. 12 and 13, another embodiment of the medical treatment of the present invention 94 includes a screw-container 96 configured to hold the two different medical agents 42 and 44. Preferably, a first chamber contains a pre-measured amount of a cleansing agent 42 and a second chamber contains a pre-measured amount of antiseptic agent. The medical kit, including the cleansing agent 42 and/or the antiseptic agent, may contain any of the agents or compositions described herein.

As illustrated in FIG. 12, the screw-container 96 is initially stored as two isolated chambers 50 and 56 which are spaced-apart by a barrier portion (a space) or lightly screwed together—about a ½ a turn. The top or first chamber 50 of the screw-container 96 can contain either female threads 100 or male threads 102. Preferably, the top chamber 50 has the female threads 100. It is designed to be filled at or near to capacity with one or more medical agents. The first chamber 50 can be of any shape. In the preferred form, the shape of the chamber is cylindrical, as shown in FIGS. 12-13. The top portion of the first chamber includes shoulders 70.

A top radial surface 104 of the first chamber contains an opening (when the bottle 46 is being stored) to allow the contents of the bottle 46 to exit the bottle 46 via an attached applicator 62, outlet, nozzle or opening when the proper pressure is exerted. The bottom radial surface 106 of the first chamber also contains an opening which is covered by foil 90 or other type of frangible membrane, protecting the medical agents from environmental elements and premature mixing or contact. These openings are provided to allow the contents 42 or 44 of the chambers 50 and 56 to mix or contact each other.

The second chamber preferably contains male threads for removably attaching the first and second chambers. The second chamber is designed to be filled at or near capacity with one or more medical agents. The second chamber can be of any shape or size, but is preferably cylindrical. The top radial surface 76 of the second chamber 56 contains an opening which is covered by an easily removable foil 90 or other frangible membrane. At least one slightly sharp blade 112 or piercing device is also provided near the screw threads. It is sharp enough to pierce and tear the foil 90 on the first chamber 50, but designed so as not to injure the user.

When the medical treatment kit is needed by the user, the foil 90 on the second chamber 56 is removed. The two chambers 50 and 56 are then screwed together. As the two chambers 50 and 56 tighten, the blade(s) 112 on the second chamber 56 pierce and tear the foil 90 coupled to the first chamber 50. This opening allows the two medical agents 42 and 44 to contact, mix and/or react-depending on the agents contained therein.

As described herein, the bottle 46 is shaken allowing the contents to thoroughly mix and interact. The resultant admixture is preferably an antiseptic shampoo 80. The applicator 62 is inverted and directed towards the wound. The bottle 46 is squeezed to dispense the proper amount of the antiseptic shampoo 80.

Referring now to FIGS. 14-17, in yet another embodiment, there is shown a 'twist' container 116 that can hold at least two medical agents 42 and 44. The main storage area 122 of the container 116 can be of any shape. However, the preferred shape of the container is cylindrical.

Figure 14:
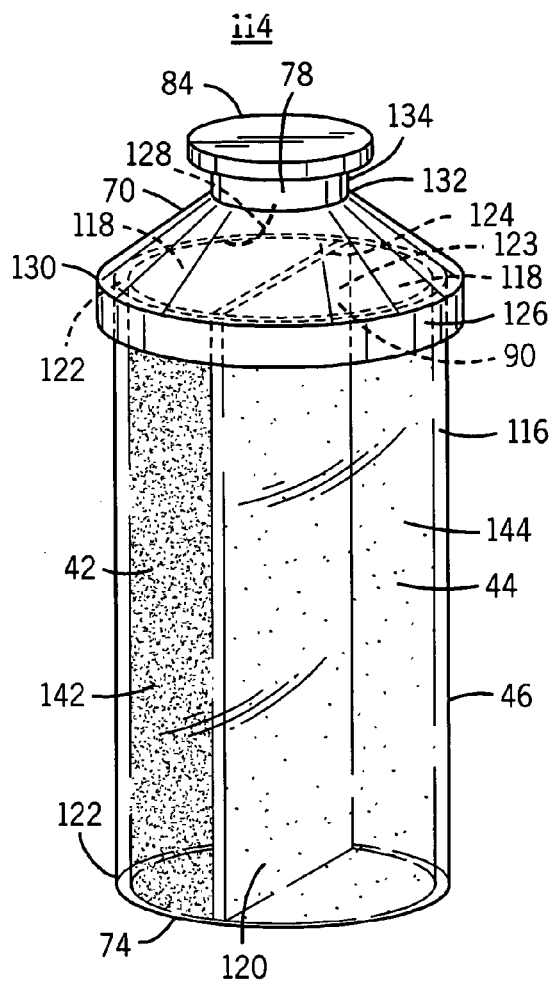
FIG. 14 is a perspective view of a further embodiment of a medical treatment kit where the container contains two chambers that are separated by a vertical wall.
Figure 15:
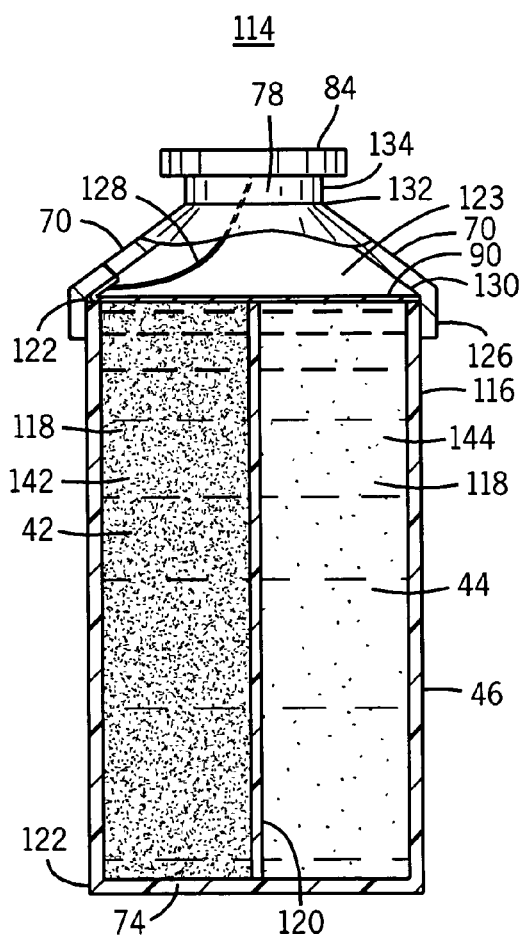
FIG. 15 is a side view of the medical treatment kit illustrated in FIG. 14.

As shown in FIGS. 14 and 15, a flexible, vertical wall 120 forms a chord 124 when viewed from the top of the container 116. The wall 120 is formed inside the main storage area 122 of the container and extends from the top to the bottom of the container 116, vertically dividing the container 116 into two separate chambers 142 and 144.

The left chamber 142 contains a pre-measured/effective amount of a cleansing agent 42 and the right chamber 142 contains a pre-measured/effective amount of an antiseptic agent 44 (or visa-versa). The cleansing agent 42 and/or the antiseptic agent 44 may be any of those described herein.

An inner portion of the top radial surface of the main storage area 122 has a breakable foil 90 or membrane. This foil 90 is sealed along the circumference of the top radial surface 126 of the main storage area 122 and also sealed along the top edge or chord 124 of the dividing wall 120. This seal also has a weakly taut but strong thread 128 connected to a cap 84 or equivalent sealing device known in the art.

Surrounding the outer circumference of the top of the main storage area 122 and permanently coupled to this circumference is an integrating chamber 123. The shape of the integrating chamber 123 is a 3-D equilateral cylindrical trapezoid. The attachment of the integrating chamber 123 to the circumference of the main storage area 122 is made with the larger of the two circular openings of the trapezoid 130. The smaller of the two openings of the trapezoid 132 has a neck or simple applicator 62 formed.

The applicator 62 is a thin cylinder with both radial surfaces open, which allows the contents of the container to flow and transfer. The top of applicator 62 has a cap 84 which can be popped off or preferably screwed off to break or rip the foil 90 and start the integrating and transfer process of the antiseptic shampoo 80. The cap 84 can be substituted with a foil, plastic or paper membrane or other sealing device known in the art.

The integrating chamber 123 issued to partially integrate or mix the two medical agents 42 and 44 when needed. The integrating chamber also protects the foil 90 from external damage or premature tearing.

Figure 16:
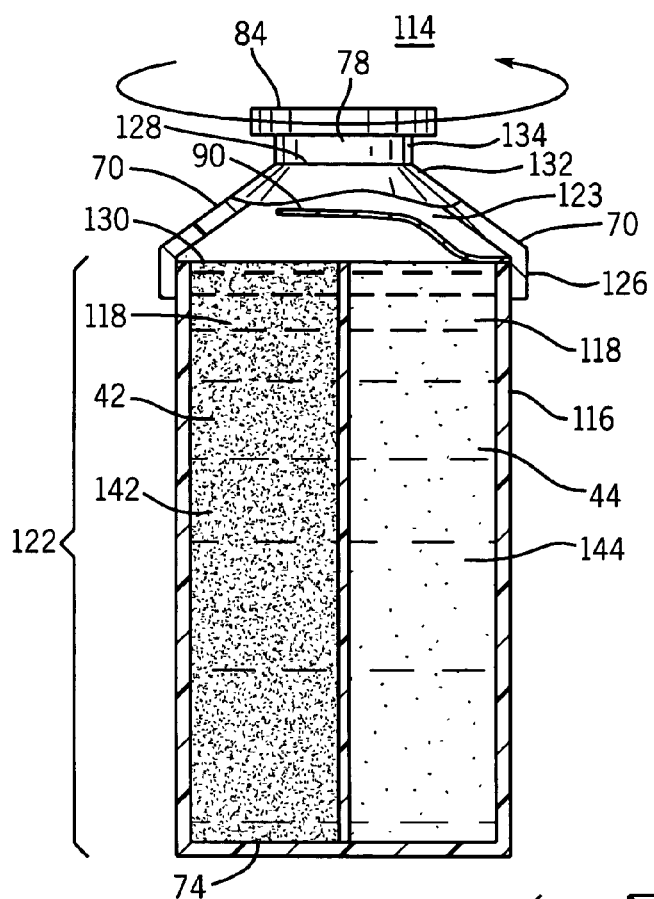
FIG. 16 is a side view of the medical treatment kit illustrated in FIGS. 14 and 15 showing a cap being twisted off to cause a foil to be torn and/or broken.
Figure 17:
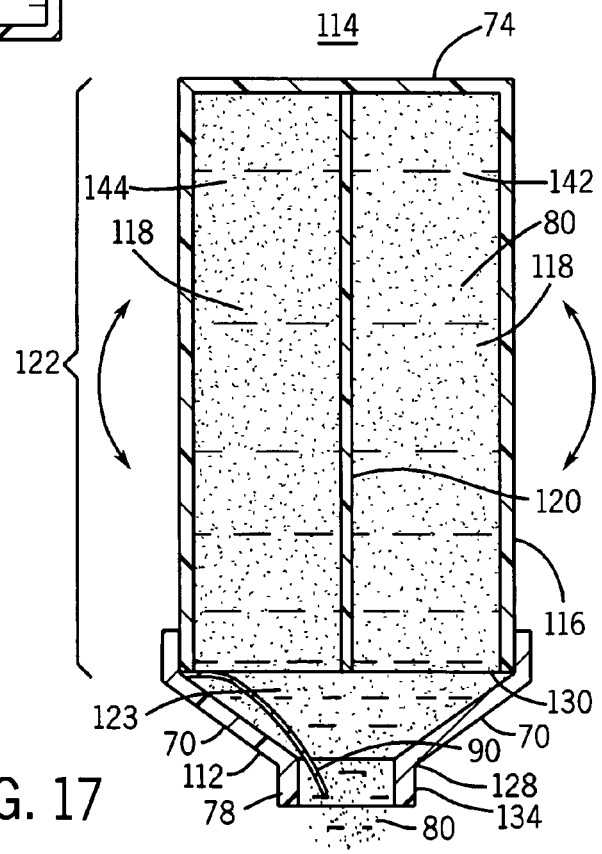
FIG. 17 is a side view of the medical treatment kit illustrated in FIGS. 14 through 16 showing the chambers being massaged and squeezed to integrate and/or mix the agents.

When the cap 84 of the 'twist' container 116 is twisted, as shown in FIG. 16, the breakable foil 90 tears allowing medical agents 42 and 44 to contact/mix. Several seconds of shaking and massaging at least partially mixes the agents 42 and 44 as shown in FIG. 17. An antiseptic shampoo 80 (or other compositional admixture) is created for treating wounds. The shampoo 80 may be directly applied to the wound using the applicator 62 (and inverting the medical treatment kit, as shown in FIG. 17).

The container illustrated in FIGS. 14-17 is advantageous in that it is much more flexible than those previously described. The flexibility allows at least a partial integration of the medical agents 42 and 44 by massaging the container.

Figure 18:
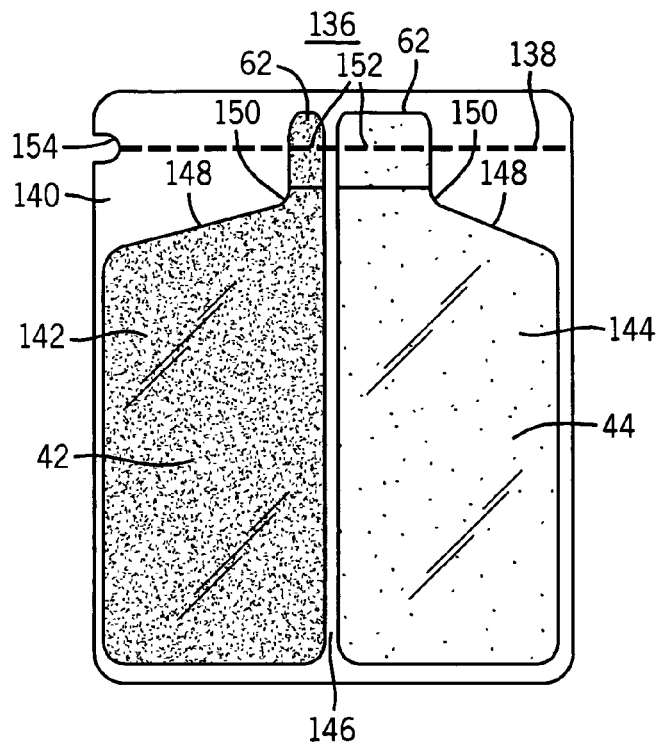
FIG. 18 is a top view of another embodiment of the medical treatment kit of the present invention showing a bag with two chambers attached by the chamber sides, with two applicators in proximity to each other, with a common tear strip.

Turning next to FIG. 18 a further embodiment of the medical treatment kit 136 of the present invention is disclosed. The kit includes a flexible bag 140 that contains two separate chambers 50 and 56 housing separate medical agents 42 and 44 or compositions. The bag may be constructed of polypropylene and/or other flexible plastic or FDA approved material know to those skilled in the art. The bag may also be constructed of foil.

The bag 140 is divided by a vertical divider into a left chamber 142 and a right chamber 144 to hold the desired medical agents 42 and 44. Preferably one chamber contains a pre-measured cleansing agent 42 and the other chamber contains a pre-measured antiseptic agent 44. The cleansing agent 42 and/or the antiseptic agent 44 may be any of those described herein. The two chambers 142 and 144 are isosceles trapezoid in shape, with the varying angled side 148 of the trapezoid on the upper portion 138 of the container. The acute angles 150 of each trapezoid chamber are placed toward the vertical divider of the two chambers 142 and 144. Each of the two chambers are preferably hermetically sealed.

At the two acute angle 150 corners of each of the chambers are preformed applicators 62, outlets or nozzles. The size of the applicators 62 will be in proportion to the viscosity of the medical agents 42 and 44 that will flow through them, will depend on the type of agents included therein and/or will depend on the application of the medical kit.

A tear strip 138 extends across the entire top of the bag 140, which also bisects 152 each of the applicators 62 of the two separated chambers 142 and 144. The tear strip is coupled to the bag or can be integrally formed into the bag. An optional notch 154 can be provided on one end of the tear strip to provide easier starting of the tear.

Figure 19:
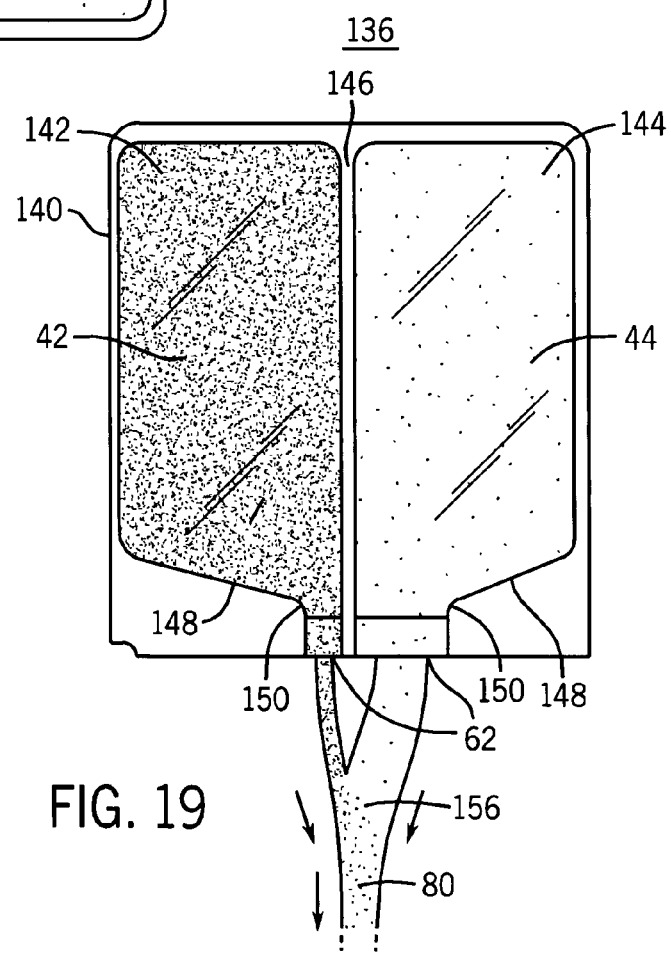
FIG. 19 is a top view of the medical treatment kit illustrated in FIG. 18, shown inverted with the tear strip removed and the two agents allowed to mix within an output stream.

When the strip is torn away, the applicators/nozzles 62 are opened, as shown in FIG. 19. The user will then turn the bag 140 upside down and squeeze the bag 140 with substantially equal pressure on both sides of each chamber. This allows at least partial mixing of the medical agents 42 and 44 forming an admixture 156 which will be applied to the wound. The admixture 156 can then be further mixed by hand directly into or on the wound.

Figure 20:
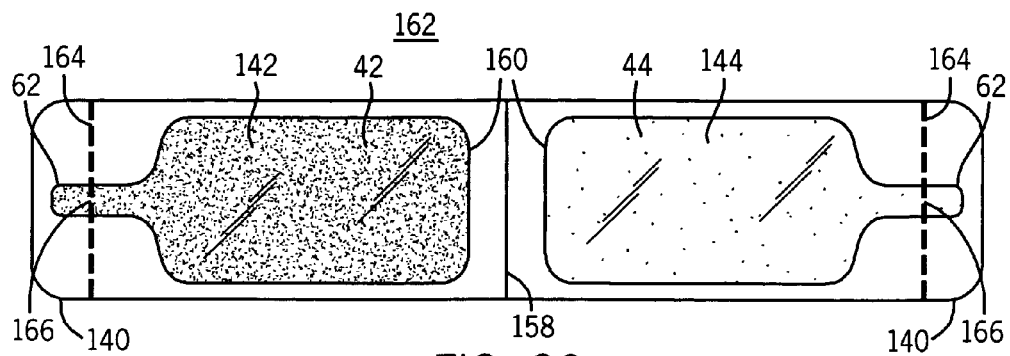
FIG. 20 is a top view of another embodiment of the medical treatment kit of the present invention showing a bag having two chambers attached at the chamber bottoms, with two applicators on opposite sides of the bag and having two distinct tear strips.

Referring next to FIG. 20, an alternate medical treatment kit 162 including a separate tear strip 164 and applicator 62 for each chamber of the bag is illustrated.

The bag 140 is divided into a left chamber 142 and a right chamber 144, with a middle sealing divider 158. The middle sealing divider 158 is designed to allow the bag 140 to be folded in half. However, instead of joining the two chambers 142 and 146 by the chambers 142 and 146 sides, the chambers 142 and 146 are joined at the bottoms of each chamber 160. Accordingly, the applicators 62 of each corresponding chamber are on opposite sides of the bag 140.

The left chamber 142 contains a pre-measured quantity of a cleansing agent 42 and the right chamber 142 contains a pre-measured quantity of an antiseptic agent 44. The cleansing agent 42 and/or the antiseptic agent 44 may be any of those described herein.

The main storage area 122 of each chambers is substantially rectangular in shape. Each rectangle has shoulders 70 on top to provide more efficient transfer of the chamber 142 and 146 contents.

With each applicator 62, there is a corresponding or mating tear strip 164 that bisects the top of each applicator at a point 166. Optionally, there can be a notch 154 (not shown) on one side of the tear strip of the bag 140 to provide easier starting of the tear. When removed, the applicator 62 is opened, allowing the contents of each chamber to mix and be applied to the wound.

Figures 21, 22:
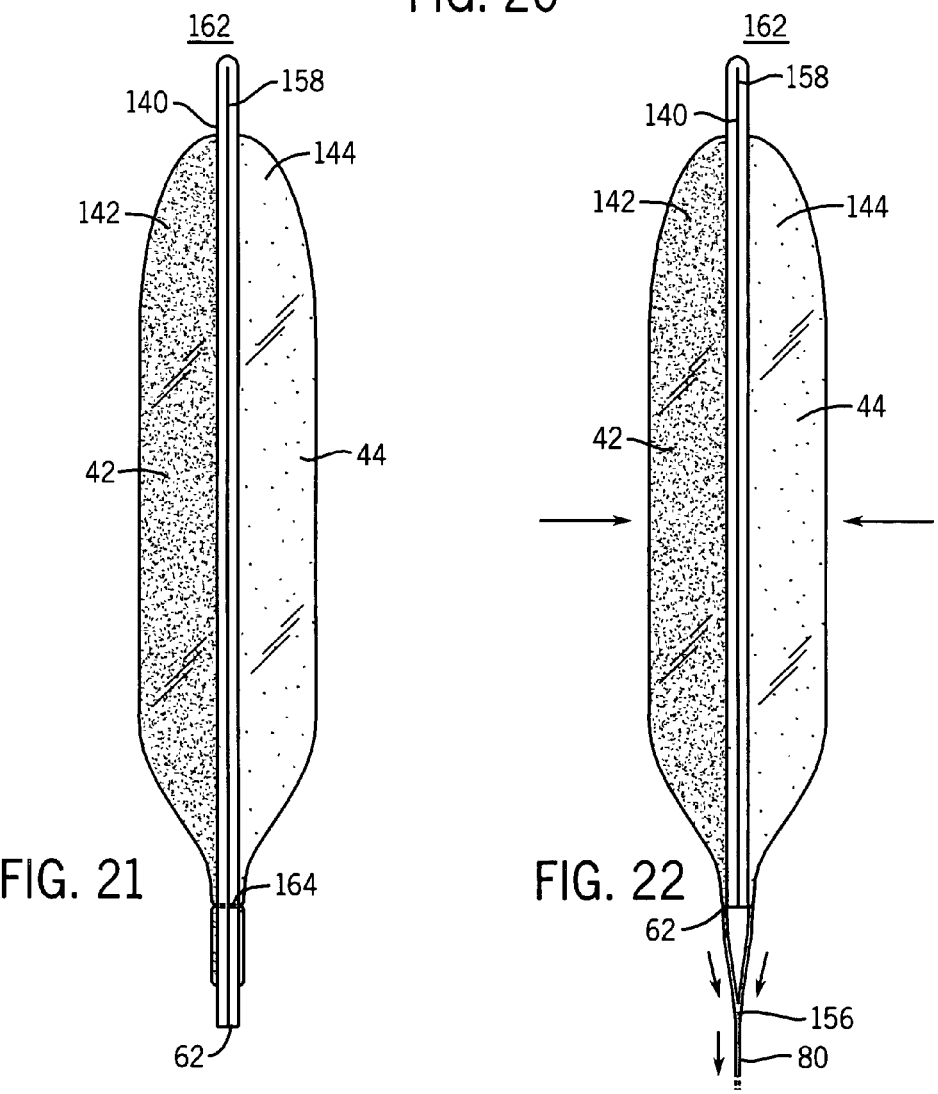
FIG. 21 is a side view of the medical treatment kit illustrated in FIG. 20 folded in half.
FIG. 22 is a side view of the medical treatment kit illustrated in FIGS. 20 and 21 showing both tear strips removed, with pressure being applied to the bag to release the agents, to mix in an output stream.

Accordingly, when ready to use, each tear strip is removed and then the bag 140 is folded in half such that the tips of the applicators 62 are next to each other, as illustrated in FIGS. 21 and 22. When squeezed in the center, this dual chamber combination at least partially mixes the two medical agents 42 and 44 outside of the chambers 142 and 146 within the output stream forming an admixture 156. The two medical agents 42 and 44 can be further mixed by the user by hand, creating an antiseptic shampoo 80. As before, the antiseptic shampoo 80 is directed to the wound via the applicator 62 of the medical treatment kit 162.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications and alterations should therefore be seen as being within the scope of the present invention.

It may therefore be appreciated from the above detailed description of the preferred embodiment of the present invention provides a medical treatment kit for cleansing a wound. The present invention also provides a method for cleaning and treating wounds that use medical agents that are inexpensive. The present invention has cleansing and antiseptic agents that are pre-measured in order to save time. The present invention has cleansing and antiseptic agents that are quick to set up. The present invention also provides a medical treatment method that is easy to implement and carry out in an emergency situation.

The medical treatment kit of the present invention is of construction which is both durable and has a long shelf life. The medical treatment kit requires little or no maintenance to be provided by the user throughout its storage lifetime. In order to enhance the market appeal of the medical treatment kit of the present invention, the kit has inexpensive agents or chemicals to thereby afford it the broadest possible market.

What is claimed is:

1. A method of treating a medical wound comprising:
providing a container formed with a first chamber and a second chamber, the first and second chambers being inseparable from each other, the first chamber of the container filled to substantially its entire capacity with a pre-measured amount of a cleansing agent and the second chamber of the container filled to substantially its entire capacity with a pre-measured amount of an antiseptic agent, the first and second chambers separated by an integrally formed, compressible bellowed diaphragm portion of the container including a barrier portion configured in a conic shape located therein, the barrier portion directly adjacent and physically contacting the cleansing agent on a first side thereof and directly adjacent and physically contacting the antiseptic agent on an opposite, second side thereof;
using at least one of the cleansing agent and the antiseptic agent to disrupt the barrier portion by compressing the diaphragm portion and applying fluid pressure to one of the two sides of the barrier portion and dislodging the barrier portion without penetrating the barrier portion, whereby the cleansing agent and the antiseptic agent are contacted; and
applying an admixture of the cleansing agent and the antiseptic agent to clean and disinfect the medical wound.

2. The method of claim 1, wherein the cleansing agent is selected from the group consisting of a shampoo, a detergent, a soap, a surfactant and combinations thereof.

3. The method of claim 1, wherein the antiseptic agent is hydrogen peroxide.

4. The method of claim 1, wherein the barrier portion comprises a stopper or disc element.

5. The method of claim 1, further comprising shaking the container after the barrier portion is disrupted.

6. A method of treating a medical wound comprising:

providing a medical treatment kit within a single housing, two enclosure container, the container having a main body of unitary construction divided into a first enclosure filled to substantially its entire capacity with a first medical composition, a second enclosure filled to substantially its entire capacity with a second medical composition and at least one barrier portion separating the first and second medical compositions within the first and second enclosures wherein the at least one barrier portion comprises an integral bellowed diaphragm portion of the container and a stopper configured in a conic shape;

applying pressure to each of the first and second enclosures, whereby at least one of the first and second medicaments dislodges the at least one barrier portion without penetrating the barrier portion;

mixing the first medical composition and the second medical composition within the main body of the kit;

applying the admixture to the medical wound; and cleaning and disinfecting the wound with the mixed first and second medical compositions and removing debris from the wound.

7. The method of claim 6, wherein the first medical composition is one of an antiseptic agent and a cleansing agent and wherein the second medical composition is the other one of an antiseptic agent and a cleansing agent.

8. The method of claim 7, wherein the antiseptic agent comprises one or more disinfecting compositions.

9. The method of claim 7, wherein the cleansing agent is selected from shampoo, soap, detergent or combinations thereof.

10. The method of claim 6, wherein at least one of the first and second medical compositions comprises an odor-controlling agent.

11. The method of claim 6, wherein the first enclosure comprises a first outlet sealed by the at least one barrier portion and wherein the second enclosure comprises a second outlet sealed by a further barrier portion.

12. The method of claim 6, wherein the mixing step includes shaking the medical treatment kit after disruption of the at least one barrier portion.

13. The method of claim 6, wherein the medical treatment kit further comprises a nozzle and wherein the applying step includes dispensing the admixture of the first and second medical compositions through the nozzle.

14. A medical treatment kit for treating a wound comprising:

a two-chamber container divided into a first chamber filled to near its capacity with an effective amount of at least one cleansing agent and a second chamber filled to near its capacity with an effective amount of at least one antiseptic agent, the first and second chambers of the container formed in a single housing component and being inseparable from each other;

a compressible bellowed diaphragm integral with the container wall and separating the first and second chambers;

a substantially impenetrable barrier portion configured in a conic shape located within the compressible diaphragm, wherein the barrier portion is directly adjacent to and contacts the cleansing agent on a first side thereof and is directly adjacent to and physically contacts the antiseptic agent on an opposite, second side thereof, preventing intermixing of the cleansing agent and the antiseptic agent, wherein the compressible diaphragm is filled to substantially its entire capacity with at least one of the cleansing agent and the antiseptic agent; and an applicator coupled to one of the first and the second chambers, wherein the cleansing agent and the antiseptic agent are mixed when the barrier portion is dislodged for cleaning and disinfecting the wound.

15. The medical treatment kit of claim 14, wherein the cleansing agent is a shampoo.

16. The medical treatment kit of claim 14, wherein the antiseptic agent is hydrogen peroxide.

17. The medical treatment kit of claim 14, wherein the main body portion further comprises a mixing chamber.

18. The medical treatment kit of claim 14, wherein the at least one barrier portion comprises a stopper.

* * * * *